United States Patent [19]
Claywell

[11] Patent Number: 5,342,317
[45] Date of Patent: Aug. 30, 1994

[54] INTRAVENOUS NEEDLE ANCHORS

[76] Inventor: Harry M. Claywell, 7044 W. Sunnyside, Peoria, Ariz. 85345

[21] Appl. No.: 134,208

[22] Filed: Oct. 8, 1993

Related U.S. Application Data

[63] Continuation-in-part of Ser. No. 887,678, May 22, 1992, abandoned.

[51] Int. Cl.$^5$ ............................................. A61M 25/02
[52] U.S. Cl. ............................... 604/179; 128/DIG. 26
[58] Field of Search ................... 604/174, 179, 180; 128/DIG. 26

[56] References Cited

U.S. PATENT DOCUMENTS

| | | | |
|---|---|---|---|
| 3,726,280 | 4/1973 | Lacount | 604/179 |
| 3,782,378 | 1/1974 | Page | 604/179 |
| 3,812,851 | 5/1974 | Rodriguez | 604/179 |
| 3,878,849 | 4/1975 | Muller et al. | 604/179 |
| 4,331,144 | 5/1982 | Wapner | 128/DIG. 26 |
| 4,445,894 | 5/1984 | Kovacs | 604/179 |
| 4,449,975 | 5/1984 | Perry | 604/179 |
| 4,569,348 | 2/1986 | Hasslinger | 604/179 |
| 4,669,458 | 6/1987 | Abraham et al. | 604/180 |
| 4,739,757 | 4/1988 | Edwards | 128/207.18 |
| 4,840,617 | 6/1989 | Osterholm | 604/179 |
| 4,844,061 | 7/1989 | Carroll | 604/179 |
| 4,846,807 | 7/1989 | Safadago | 604/179 |
| 5,009,227 | 4/1991 | Meuustad | 128/DIG. 26 |
| 5,037,397 | 8/1991 | Kalt | 604/179 |
| 5,205,832 | 4/1993 | Tuman | 604/179 |

Primary Examiner—Paul J. Hirsch

[57] ABSTRACT

An anchor band is positionable about the limb or head of a patient undergoing an intravenous procedure. Hospital personnel may continue to use their standard practices of maintaining intravenous angiocatheter's and tubing in position by use of adhesive tape. The anchor band, however, acts as a buffer between the adhesive tape and the patients skin. Thereafter, normal hospital procedures which require the removal, reapplication, and, again, removal of adhesive tape, because of adjustments and accommodations to the intravenous angiocatheter and tubing, will cause no irritation or damage to the patient's skin since the adhesive will be applied and removed, and reapplied to the anchor band rather than directly to the person's skin. Non-slip pads are used to avoid rotation or slippage and are spaced on the underside of the band such that the portion of the band adjacent the I.V. angiocatheter is pulled into a flush relationship with the patients skin to prevent deviation or exertion of upward forces on the exposed end of the angiocatheter.

13 Claims, 1 Drawing Sheet

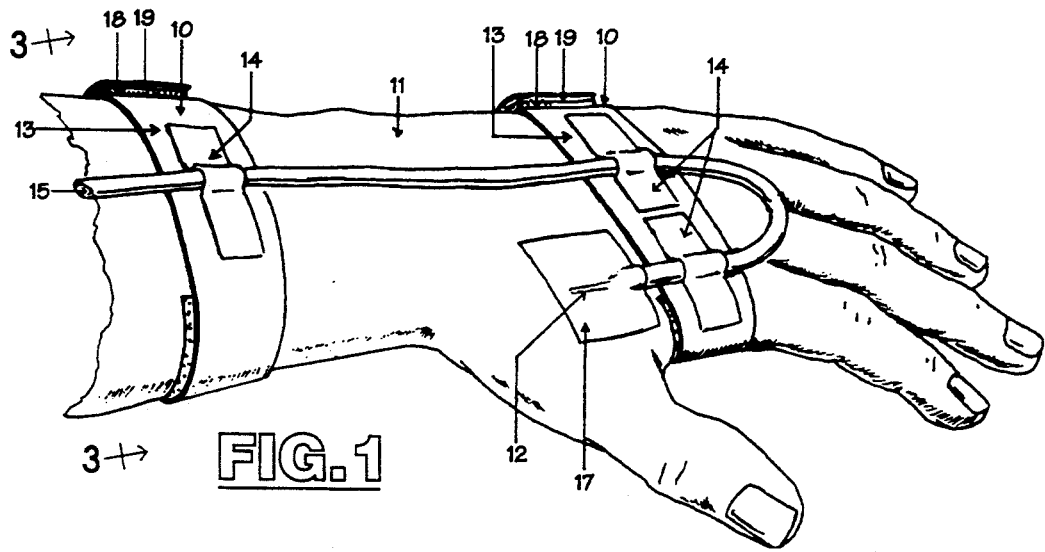
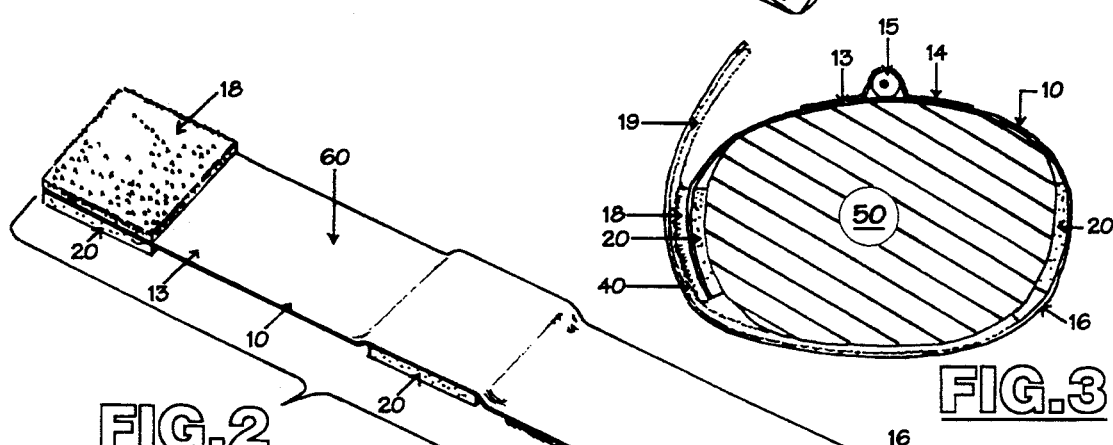
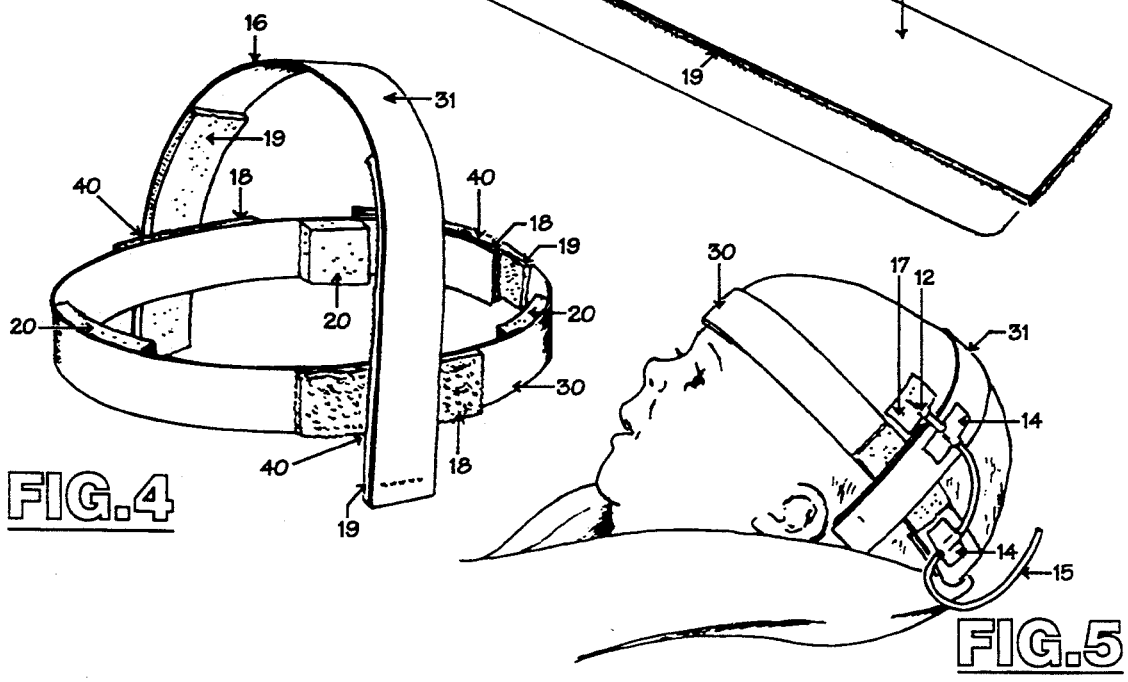

INTRAVENOUS NEEDLE ANCHORS

This application is a Continuation-In-Part of U.S. application Ser. No. 07/887,678, filed May 22, 1992, now abandoned.

BACKGROUND

1. Technical Field of the Invention

The invention relates to means for preventing the inadvertent withdrawal of intravenous (I.V.) needles and the like. In particular, the invention allows hospital personal to continue the use of adhesive tape to hold needles and I. V. tubes in position while precluding the direct application of adhesive tape to the skin of the patient.

2. Prior Background Art

Damage can be done to the skin of infants and older persons receiving intravenous solutions. This damage comes about by repeated application and removal of adhesive tape used in maintaining the I.V. needle and tubing in position. Typical sites of such damage include the head of an infant and the hand or arm of a person undergoing I.V. procedures in the hospital.

The I.V. needle and tube must be anchored to prevent inadvertent removal of the needle from the patient. The tube is generally anchored at two points adjacent the needle, using adhesive tape to hold the tube in position on the person. In a recent case in which an infant was receiving an intravenous solution in a vein in its head, the removal of the adhesive tape ripped the child's tender skin and tore its ear from its head. Older persons with fragile skin are prone to damage caused by the removal of adhesive tape. The application of safe intravenous procedures with burn patients is similarly complicated.

The prior art is replete with devices for holding I.V. tubing and needles in position on a person's limb. However, all of these devices known to the inventor are complicated and depart from standard practice of maintaining needles and tubing in position with a short length of adhesive tape. It is the object of the present invention to permit hospital staff to maintain their long time practice of utilizing adhesive tape, a material readily available to a hospital's health care personnel, while providing a buffer of protection between the adhesive material of the tape and the person's skin.

SUMMARY DESCRIPTION OF THE INVENTION

The invention may be summarized as an anchor band useful for administering I.V. therapy. It includes a band of material having a first end and a second end. There is an inside surface and an outside surface. It has a length sufficient to permit the band to overlappingly encompass a patient's body part adjacent a site at which I.V. therapy is to be administered. A pair of resilient pads are affixed to the inside surface of the band in a specifically selected, spaced apart relationship. The resilient pads are generally diametrically opposite one another when the band encompasses the body part adjacent the I.V. therapy site.

Because of the diametric relationship of the pads, the band has a first portion between the pair of resilient pads which lies in a flush relationship with the skin surface of a patient adjacent the body site at which the I.V. therapy is to be administered. At least one of the resilient pads has a non-slip surface in intimate contact with the skin of a patient when the band overlappingly encompasses the patient's body part. Preferably the anchor band is of a material which is inelastic.

The invention may also be summarized as an anchor band for use in maintaining intravenous (I.V.) needles and tubing in position on a patient. The anchor band comprises a first flexible band having a first end and a second end. Included is an upper surface and a lower surface. The length is sufficient to encompass the body site at which an I.V. needle enters a patient. Provided are means for maintaining the first flexible band encompassing the body site with the upper surface thereof generally exposed. The lower surface is generally in contact with the patient's skin. Preferably, the first flexible band is a thin gas permeable, hypoallergenic, soft cloth type material generally free of elastic properties. It is selected to have an upper surface to which adhesive tape will readily adhere and a lower surface which is a skin contacting, adhesive-free surface. The length of the first flexible band is sufficient to overlappingly encompass the body site. The bands are wider than most hospital tapes which is desirable for ease of taping and the nurse is able to use a multi-angle taping approach. The invention is made gas-permeable to allow perspiration to evaporate and cool air to reach the patients skin for comfort during use.

The means for maintaining the first flexible band encompassing the body site comprises a hook and loop fastener comprised of a hook part and a loop part. The hook part is affixed to the first end of the first flexible band on its upper surface. This upper surface will not contact the patient's skin. The second loop part is affixed to the second end of the first flexible band on its lower surface. The lower surface of the first flexible band includes a non-slip surface.

This non-slip surface comprises the skin contacting faces of a first and a second resilient pad affixed to the lower surface. These pads each comprise a hypoallergenic, open-cell, non-corrosive foam affixed to the lower surface. The first resilient pad is affixed to the first end of the first flexible band on its lower surface. The second resilient pad is affixed to the lower surface a selected distance from the first resilient pad. The distance is selected such that the portion of the first flexible band joining the first and the second resilient pads lies in intimate contact with the patient's skin by pulling the upper surface into a flush relationship with the patients skin when the first flexible band overlappingly encompasses the body site of the I.V.

In a presently preferred, argumented embodiment of the invention, the first flexible band has a length sufficient to encompass the head of an infant, the body site at which an I.V. needle enters an infant patient. There is a second flexible band which has a length sufficient to generally encompass transversely the top of the infant's head. The second flexible band, like the first flexible band, is a very thin gas permeable, hypoallergenic, open-celled, soft cloth type material generally free of elastic properties. Each has an upper surface to which adhesive tape will readily adhere, as well as a lower surface which is skin contacting and adhesive-free. The invention is made gas-permeable to allow perspiration to evaporate and let cool air to reach the patients skin for comfort during use. The bands are established as being wider than most standard hospital tapes and are designed to be wide enough to permit a multi-angle approach to taping. Hook and loop fastening means are utilized for coupling the second flexible band to the first flexible band.

The lower surface of the second flexible band includes a non-slip surface of open-cell, hypoallergenic, non-corrosive foam.

The invention may be summarized in terms of the steps taken to produce it. For example, the invention is an anchor band for use in maintaining intravenous (I.V.) needles and tubing in position on a patient, the anchor band being produced by the process of:

selecting a thin, flexible, gas permeable, non-elastic, hypoallergenic soft cloth type material for use as a non-vessel-constricting band for encompassing the body site of a patient at which I.V. therapy is to be administered;

further selecting the material to be non-adhering to the skin of a patient but having a surface to which adhesive tape will readily adhere;

forming a flexible band of the material, giving the band sufficient length to overlappingly encompass the body site at which an I.V. needle enters a patient's blood vessel;

applying the hook fastener of a hook-and-loop fastener assembly to a first end of the band on the non-skin contacting surface of the band, the band having a first surface which will contact a patient's skin and a second surface which will be non-skin-contacting;

applying the loop fastener of a hook-and-loop fastener assembly to a second end of the band on the surface of the band which contacts a patient's skin when the band encompasses an I.V. therapy body site;

providing the band with non-slip surfaces for contacting the skin of a patient when the band generally encompasses the body site.

selecting the non-slip surface to be skin contacting faces of a first and a second resilient pad to be affixed to the first, skin-contacting surface;

selecting the first and second pad to be an open-cell, hypoallergenic, non-corrosive foam;

affixing the first resilient pad to a first end of the first flexible band on the first, skin contacting surface thereof;

affixing the second resilient pad to the first, skin-contacting surface a specifically selected distance from first resilient band; and selecting the distance such that the portion of the flexible band joining the first and the second resilient pad lies in intimate contact with the patient's skin by using the resilient pads to pull the upper surface into a flush relationship with the patients skin when the first flexible band overlappingly encompasses the body site.

To produce the anchor band for use with an infant, the step of forming the band, hereinafter the first band, includes the step of giving the first band sufficient length to encompass the head of an infant, the infant's head being the body site of an I.V. needle.

The anchor band is produced by the further steps of:

providing a cross-member band of the material, giving the cross-member band sufficient length to generally encompass the crown of the infant's head and overlap the first band; and adding first and second hook fasteners to the first, non-skin-contacting surface of the first band in selected, spaced apart positions on the first band;

selecting the spaced apart positions so as to position one of each of the first and second hook fasteners approximately adjacent to an ear of the infant's head to be encompassed by the first band;

providing first and second loop fasteners at first and second ends respectively of the cross-member band for forming hook-and-loop fastener assemblies when the cross-member band encompasses the crown of an infant's head and the first and second ends of the cross-member band overlap the first band encompassing the infant's head. The hook and loop fastener provides the ability to adjust the flexible band for length and angle of application.

One may undertake the further step of providing the cross-member band with non-slip surfaces for contacting the crown of the infant's head.

BRIEF DESCRIPTION OF THE DRAWINGS

FIG. 1 illustrates a patient's hand and wrist showing two innovative intravenous anchor bands in use to maintain an I.V. needle and tubing in position.

FIG. 2 is a perspective view of the I.V. anchor band of the invention.

FIG. 3 is a cross-sectional view of a person's arm showing the I.V. anchor band in position. Adhesive tape is shown maintaining an I.V. tube on the anchor band.

FIG. 4 is a perspective drawing of two I.V. anchor bands. A first anchor band is employed as a head-band about the head of an infant. The second is a cross-band which goes across the top of the head of the infant.

FIG. 5 illustrates the use of the head-band and cross-band of FIG. 4 on the head of an infant to maintain an I.V. needle and an I.V. tube on the infant's head.

DETAILS OF BEST MODE FOR CARRYING OUT THE INVENTION

For purposes of promoting an understanding of the principles of the invention, reference will now be made to the embodiments illustrated in the drawings and specific language will be used to describe same. It will nevertheless be understood that no limitation of the scope of the invention is thereby intended. Alterations and modifications of the illustrated device are contemplated, as are such further applications of the principles of the invention as would normally occur to one skilled in the art to which the invention pertains.

A frequent situs for an I.V. needle is at the back of a patient's hand. See FIG. 1. A bioclusive dressing 17 covers the needle 12 and the wound site. Dressing 17 is transparent, "breathes" and is readily removed without skin damage. I.V. needle 12 is inserted into a vein in the hand 11 of a patient. Attached to the I.V. needle is an I.V. tube 15 which goes to the source (not shown) of medication or solution being infused into the patient. Under prior art hospital practices, strips of adhesive tape 14 would be applied across I.V. tubing 15 and adhered to the patient's skin to maintain tubing and needle in place. Thus, each time needle 12 had to be adjusted or some other accommodation made, adhesive tape 14 was pulled from the person's skin, the needle repositioned as required, and new adhesive tape applied.

In general, under prior art techniques, fresh adhesive tape would be applied to approximately the same area of the patient's skin many times during the course of an on-going I.V. procedure. It was the repeated application and removal of adhesive tape from such areas of skin which led to skin damage and painful abrasions.

The use of the invention represents an improvement in the prior art technique. As shown in FIG. 1, an anchor band 10 is positioned on the patient's arm adjacent the site at which I.V. needle, and in close proximity thereto, of the path of I.V. tube 15. Bands 10 are intended to maintain themselves in position on the patient's arm or leg or other bodily part at which an I.V. procedure is initiated. As with the prior art, health care personnel maintain the needle 12 and tubes 15 in position using adhesive tape 14. However, in this instance, adhesive tape 14 is applied to bands 10, and not directly to the patient's skin.

With bands 10 as an intervening buffer between the adhesive tape and the patient's skin, repeated applications, removals, and reapplications of adhesive tape may be made without damage to the patient's skin. The invention is made gas-permeable to allow perspiration to evaporate and cool air to reach the patients skin for comfort during use.

An I.V. procedure anchor band 10 is drawn in perspective in FIG. 2. The band 10 is fabricated of flexible strapping 16. Strapping 16 is preferably a cotton web and has the appearance and feel of a soft cloth belt. Such strapping or belting is referred generically herein as webbing. Webbing has a surface 13 to which adhesive tape will readily adhere and from which the tape may be readily withdrawn. The bands are wide enough to allow for a multi-angle approach to taping the needle and tubing, the bands being established as wider than most hospital tapes.

Webbing 16 is a thin lightweight, gas permeable and hypoallergenic material generally free of elastic properties. Freedom of elastic properties is an important characteristic of webbing 16 to avoid constriction of a blood vessel by band 10. Constriction of a blood vessel being used for I.V. therapy can cause the I.V. fluid to infiltrate into the patient's body tissues which can result in severe conditions dreaded by health care personnel as well as the patient.

Webbing 16 will be maintained in position on a person's limb by use of hook and loop fasteners. Thus, for example, a hook fastener 18 is shown on the leftmost end of webbing 16 in FIG. 2. At the rightmost end of webbing 16, and on the side opposite that to which hook fastener 18 is adhered, is loop fastener 19. Placing loop fastener 19 on this side of webbing 16 assures that only a soft, non-skin-eroding contact will be made with the skin of the patient. Hook fastener 18, being on the outside surface of band 10 never has its rough surface drawn into contact with the patient's skin. Used in this manner, with hook and loop fasteners 18 and 19 positioned as described, band 10 provides a closure band which is variable in size, angle of application has a secure fastening, and is non-erosive to the skin of a patient. Non-slip pads 20 are affixed to the same side of webbing 16 as is loop fastener 19 in FIG. 2.

The lack of elasticity as well as pads 20 allow band 10 to be a stabile circumferencing band. For example, a first pad 20 is placed near, say one-eighth inch removed from, the end of band webbing 16. A second pad 20 is placed on webbing 16 a distance removed from the first pad, about three and one-half inches.

These measurements are set out for purposes of exposition and not of limitation. In practice, resilient pads 20 are spaced so as to be generally diametrically opposite each other when webbing 16 encompasses a person's limb adjacent an I.V. therapy site. See FIG. 3. The reason for so spacing pads 20 is that that portion of webbing 16 comprising area 60 where I.V. tubing 15 is attached in FIG. 3, will be pulled into a flush relationship with the skin where the upper surface of the band will be flush with the patient's skin. With a flush taping surface assured there will be no upward force applied on either an I.V. tube or an I.V. needle taped in position in area 60 of webbing 16.

In use, anchor band 10 is wrapped about a patient's limb, shown in cross-section in FIG. 3; and hook and loop fasteners, 18 and 19, are joined to form the assembled fastener 40. Any excessive lengths of the band may be trimmed without leaving frayed edges. Pads 20 bear upon the person's skin. A pad 20 is a soft, resilient pad, which presents a non-slip surface to the skin and therefore inhibits the rotation of band 10 about the limb of the person. Band 10 is positioned close to the site at which needle 12 is inserted into the vein of a person. See FIG. 1. I.V. tube 15 is positioned across two or more such bands and maintained in position by adhesive tape 14 which readily adheres to the surface 13 of each band 10.

Webbing 16 is, for example, a 1300 weave twill tape of one-hundred-percent cotton. This tape is a thin, gas permeable, non-irritating, hypoallergenic, and will not adhere to the patient's skin. However, adhesive tape 14 readily adheres to this material and, in most cases adheres to the cotton twill better than it will to a patient's skin. The bands are wide enough to allow for a multi-angle approach to taping the needle and tubing, the bands being established as wider than most hospital tapes.

The area 60 of webbing 16, between non-slip pads 20, is proximal to needle 12 and, by designed placement of pads 20 and the inelasticity of webbing 16, lies in a flush relationship flush with the patient's skin. See discussion above. Because area 60 is flush to the skin and conforms to the extremity to which band 10 is applied, webbing 16 will exert no upward pressure on needle 12 nor cause the needle to deviate from its approach to the patient's vein. This obviates infiltration of the I.V. fluid into body tissue.

Pads 20 are open/celled, hypoallergenic, steam/pressure autoclavable, adhesive backed, non-corrosive foam, say, for example three-sixteenth inch thick, to cushion band 10 and inhibit rotation of the band and also to pull the band into a flush relationship with the patients skin. To be preferred is a white open cell polyurethane foam coated on one side with a hypoallergenic pressure sensitive adhesive. It is understood that the adhesive face is applied to band 10 and is never applied to the patient's skin.

Adhesive tape 14, by its adherence to surface 13 of band 10, will maintain the I.V. tubing 15 in position. When the tubing must be cleared, or the needle removed and repositioned, or otherwise accommodated, tape 14 will be readily removed from surface 13 of band 10. Thus, the persons's skin is not subject to tears or other damage by repeated applications and removals of adhesive tape to and from their skin.

In the drawing of FIG. 1 two bands 10 in fairly close juxtaposition are shown. This is in accord with generally accepted hospital practice which requires the application of multiple pieces of adhesive tape in the vicinity of I.V. needle 12 to maintain the needle and tubing in position on the patient. A first band 10 secures tubing 15 adjacent needle 12 at the site at which the patient's blood vessel is punctured. A second band 10 is placed, preferably, adjacent the bulge of the patient's forearm. It should be noted that when needle 12 is removed from the patient's vein and a gauze covering placed over the bleeding puncture site, one of the bands 10 may be applied tightly over the gauze covering as a pressure dressing. The puncture site may be thereafter assessed without risk of damage to delicate tissue.

The use of the invention may be further extended so as to protect the delicate, thin skin covering an infant's head. When an infant is the subject of an intravenous procedure, the veins in the head are generally the most prominent and accessible. This skin is readily damaged upon removal of adhesive used to maintain the I.V. needle in position. To protect the infant's skin, an assembly of two bands such as band 10 of FIG. 2 may be employed the bands being wider than most common hospital tape allow ease of taping and the use of the multi-angle taping approach. The assembly is shown in FIG. 4. There is a head-band 30 made of webbing 16 and equipped with a hook and loop fastener 40 for adjustable placement about an infant's head. A cross-band 31 is adjustably fastened to head-band 30 by means of one or more hook and loop fasteners 40. Cross-band 31 will be positioned across the top of an infant's head adjacent the site at which an I.V. needle is inserted into the infant's scalp.

The use of the assembly of FIG. 4 is illustrated in FIG. 5. Here, an infant 60 has an I.V. needle 12 inserted into his scalp vein. Head-band 30 is adjusted to fit about the infant's head. Cross-band 31 is drawn across the top of the scalp adjacent to the site at which needle 12 is inserted. I.V. tubing 15 is draped across the top of cross-band 31 and maintained in position there with adhesive tape 14. The I.V. tubing 15 is conducted downward to where it crosses head-band 30, and is again maintained in position there with an additional strip of adhesive tape 14. No adhesive is applied directly to the scalp of the infant. Non-slip pads 20 are applied at selected positions on band 30 and cross-band 31 to maintain the head-band comfortably in position and inhibit any slippage between the bands and the child's head the flush taping surface required. See FIG. 4.

What has been disclosed is an anchor band positionable about the limb or head of a patient undergoing an intravenous procedure. Hospital personnel may continue to use their standard practices of maintaining intravenous needles and tubing in position by use of adhesive tape. The anchor band, however, acts as a buffer between the adhesive tape and the patient's skin. Thereafter, normal hospital procedures which require the removal, reapplication, and, again, removal of adhesive tape, because of adjustments and accommodations to the intravenous needle and tubing, will cause no irritation or damage to the patient's skin since the adhesive will be applied and removed, and reapplied to the anchor band rather than directly to the person's skin. In addition to a surface which accepts adhesive tape, the band provides a non-slip surface to inhibit rotation or slippage of the band when it is applied to a person's limb. Simple closure means, for closing the band upon a limb are disclosed, for example hook and loop fasteners.

Those skilled in the art will conceive of other embodiments of the invention which may be drawn from the disclosure herein. To the extent that such other embodiments are so drawn, it is intended that they shall fall within the ambit of protection provided by the claims herein.

Having described the invention in the foregoing description and drawings in such clear and concise manner that those skilled in the art may readily understand and practice the invention:

That which is claimed is:

1. An anchor band useful for administering I.V. therapy comprising:

a band of material having a first end and a second end, an inside surface and an outside surface and a length sufficient to permit said band to overlappingly encompass a patients body part adjacent a site at which I.V. therapy is to be administered;

said band made of a soft cloth type material being thin and producing the result of a flush with the skin taping surface and to avoid elevation or deviation of the inserted I.V. needle;

a pair of resilient pads affixed to said inside surface of said band in a specifically selected, spaced apart relationship key to providing the flush with the skin relationship of said band;

said resilient pads being generally diametrically opposite one another when said band encompasses said body part adjacent said I.V. therapy site.

2. The anchor band of claim 1 wherein said band has a first portion between said pair of resilient pads lying in a flush relationship with the skin surface of a patient adjacent the body site at which said I.V. therapy is to be administered when said band overlappingly encompasses said patient's body part.

3. The anchor band of claim 2 wherein said material is an inelastic, thin, soft, finely woven cloth material.

4. The anchor band of claim 1 wherein said resilient pads have non-slip gas permeable surfaces in intimate contact with the skin of a patient when said band overlappingly encompasses said patient's body part.

5. The anchor band of claim 1 wherein said material is an inelastic, thin, soft, finely woven cloth material.

6. An anchor band for use in maintaining intravenous (I.V.) needles and tubing in position on a patient comprising, a first flexible band having a first end and a second end, an upper surface and a lower surface, and a length sufficient to encompass the body site at which an I.V. needle enters a patient;

means for maintaining said first flexible band encompassing said body site with the upper surface generally exposed and said lower surface generally in contact with the skin of said patient;

said first flexible band is a thin, gas permeable, hypoallergenic, soft cloth type material generally free of elastic properties selected to have a said upper surface to which adhesive tape will readily adhere and a said lower surface to be a skin contacting, adhesive free surface;

said length of said first flexible band is sufficient to overlappingly encompass said body site; and said means for maintaining said first flexible band encompassing said body site comprises a hook and loop fastener;

said hook and loop fastener being comprised of a first hook part and a second loop part;

said first hook part being affixed to said first end of said first flexible band on said upper surface free of contact with said patient's skin; and said second loop part being affixed to said second end of said first flexible band on said lower surface; and said hook and loop fastener providing the ability to adjust the flexible band for length and angle of application;

wherein said lower surface of said first flexible band includes non-slip resilient foam pad surfaces to provide for non-rotation or slippage of said band;

wherein said non-slip surfaces comprise skin contacting faces of a first and a second resilient pad affixed to said lower surface, said first and second pads comprising an open-cell, hypoallergenic, non-corrosive foam affixed to said lower surface;

said first resilient pad being affixed to said first end of said first flexible band on said lower surface thereof;

said second resilient pad being affixed to said lower surface a specifically selected distance from said first resilient pad;

said distance being selected such that the portion of said first flexible band joining said first and said second resilient pad is pulled into a flush relationship with said patient's skin when said first flexible band overlappingly encompasses said body site.

7. The anchor band of claim 6:

said first flexible band having a length sufficient to encompass the head of an infant, the body site at which an I.V. needle enters an infant patient;

a second said flexible band having a length sufficient to generally encompass transversely the top of the head of said infant;

said second flexible band, like said first flexible band, being a thin, gas permeable, hypoallergenic, soft cloth type material generally free of elastic properties and having a said upper surface to which adhesive tape will readily adhere, and a said lower surface, skin contacting and adhesive-free; and hook and loop fastening means for coupling said second flexible band to said first flexible band.

8. The anchor band of claim 7 wherein said lower surface of said second flexible band includes non-slip surfaces of open-cell, hypoallergenic, non-corrosive foam.

9. An anchor band for use in maintaining intravenous (I.V) needles and tubing in position on a patient, said anchor band being produced by the process of:

selecting a flexible gas permeable, non-elastic, hypoallergenic material for use as a non-vessel-constricting band for encompassing the body site of a patient at which I.V. therapy is to be administered;

said band being made of a soft cloth type material being thin and producing the result of a flush with the skin taping surface and to avoid elevation or deviation of the inserted I.V. needle;

further selecting said material to be non-adhering to the skin of a patient but having a surface to which adhesive tape will readily adhere;

forming a flexible band of said material, giving said band sufficient length to overlappingly encompass said body site at which an I.V. needle enters a patient's blood vessel;

providing said band with a non-slip surface for contacting the skin of a patient when said band generally encompasses said body site;

selecting said non-slip surface to be skin contacting faces of a first and a second resilient pad to be affixed to said first, skin-contacting surface;

affixing said first resilient pad to a first end of said first flexible band on said first, skin contacting surface thereof;

affixing said second resilient pad to said first, skin-contacting surface a specifically selected distance from first resilient pad; and selecting said distance such that the portion of said flexible band joining said first and said second resilient pad is pulled into a flush relationship with said patient's skin when said first flexible band overlappingly encompasses said body site.

10. The anchor band of claim 9 further including the step of selecting said first and second resilient pad to be an open-cell, hypoallergenic, non-corrosive foam to provide for non-rotation or slippage of said band.

11. The anchor band of claim 9 further comprising the step of:

applying the hook fastener of a hook-and loop fastener assembly to a first end of said band on the non-skin contacting surface of said band, said band having a first surface which will contact a patient's skin and a second surface which will be non-skin-contacting;

applying the loop fastener of a hook-and-loop fastener assembly to a second end of said band on the surface of said band which contacts a patient's skin when said band encompasses an I.V. therapy body site; and said hook and loop fastener providing the ability to adjust the flexible band for length and angle of application.

12. The anchor band of claim 9 wherein the step of forming said band, hereinafter said first band, includes the step of giving said first band sufficient length to encompass the head of an infant, the infant's head being the body site of an I.V. needle, and said anchor band is produced by the further step of:

providing a cross-member band of said material, giving said cross-member band sufficient length to generally encompass the crown of said infant's head and overlap said first band; and adding first and second hook fasteners to said first, non-skin-contacting surface of said first band in specifically selected, spaced apart positions on said first band;

selecting said spaced apart positions so as to position one of each of said first and second hook fasteners is approximately adjacent to an ear of the infant's head to be encompassed by said first band; and providing first and second loop fasteners at first and second ends respectively of said cross-member band for forming hook-and-loop fastener assemblies when said cross-member band encompasses the crown of an infant's head and said first and second ends of said cross-member band overlap said first band encompassing said infant's head.

13. The anchor band of claim 12 produced by the further step of providing said cross-member band with a soft non-slip, gas permeable surface for contacting the crown of said infant's head.

* * * * *